United States Patent [19]

Moore

[11] Patent Number: Plant 6,793

[45] Date of Patent: May 9, 1989

[54] ROSE PLANT/ MORYELRUG

[75] Inventor: Ralph S. Moore, Visalia, Calif.

[73] Assignee: Sequoia Nursery, Visalia, Calif.

[21] Appl. No.: 129,785

[22] Filed: Dec. 7, 1987

[51] Int. Cl.[4] ..... A01H 5/00

[52] U.S. Cl. ..... Plt./1

[58] Field of Search ..... Plt./1

*Primary Examiner*—James R. Feyrer

[57] ABSTRACT

This invention relates to a new and distinct variety of hybrid rugosa rose plant primarily identified by its yellow buds and double flowers of medium yellow color.

1 Drawing Sheet

1

The present invention relates to a new and distinct variety of hardy shrub type rose plant of the Hybrid Rugosa class; the variety being primarily characterized—as to novelty—by the slender yellow buds and double yellow flowers.

The variety is further characterized by:

An abundance of bloom, with flowers usually borne several to the stem in clusters of 5 to 7 or more. Quite fragrant.

A plant which is vigorous, of rounded to spreading shape with large semi-glossy to matt foliage with pointed leaflets; the buds and flowers being similar in form to Orangeade—floribunda, not patented.

The plant, which has a normal height of about 5 feet, with a spread of 6 to 7 feet, can easily be maintained at lesser height by occasional trimming.

A plant which grows and blooms satisfactorily in the garden, is good for growing in the shrub border, as an individual flowering shrub or as a hedge.

The present variety of Hybrid Rugosa was originated by me at Sequoia Nursery, located at Visalia, Calif., under conditions of careful control and observation, as a cross between Golden Angel (U.S. Plant Pat. No. 4,028, miniature) as the seed parent and Belle Poitevine, a hybrid rugosa—not patented, as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers. Note: Color can vary with the weather and time of year, being darker than photo in cooler weather.

Referring now specifically to the new and distinct variety of hybrid rugosa rose plant, the following is a detailed description thereof in outline; all major color plate identifications being by reference to the British Colour Council Horticultural Colour Chart, except where common terms of color definition are employed.

Type: Hardy; bushy; rounded; seedling; outdoors; garden decoration; landscape; shrub.

Class: Hybrid Rugosa (shrub). Variety identification: Moryelrug (Commercial synonym: Topaz Jewel).

Flowers borne: Sometimes singly but usually several together on short, wirey stems and on tips of new shoots.

Quantity of bloom: Abundant all season (spring to fall).

Bud:

2

*Peduncle.*—Medium length; slender but sturdy; erect; medium green, with numerous short prickles and some small hair-like apendages.

*Before calyx breaks; size.*—Large.

*Form.*—Pointed, with few to several small foliaceous apendages and hairs on surface of bud; with foliaceous parts extending beyond the tip of the bud equal to less than one-half of its length. Color— medium green, occasionally tinted with bronze. As calyx breaks, color greenish yellow and often tinted with red. Opening: opens well in all weather.

Bloom:

*Size when fully open.*—Large, averaging about 3 to 3½".

*Petalage.*—Double — averaging about 20–30 (or more) petals, arranged regularly plus several small petaloids.

*Form.*—Cupped with petals rolled loosely outward and downward at maturity. Open flowers usually show stamens.

Petals: Fairly thick; satiny on inside and on outside surface.

*Shape.*—Outside petals, broad lanceolate (nearly round) with rounded tip; intermediate — broad lanceolate with nearly round or short acute tip; inside — lanceolate with acute tip.

Color: Newly opened flower from a plant grown outdoors (November 1987), Visalia, Calif.

*Outside surface.*—Outside surface — near Lemon Yellow 4/2 (or deeper) on basal ⅓ to ½ of petal, becoming lighter yellow, (near Lemon Yellow 4/3) near tip. Inside surface — small area at base near Lemon Yellow 4/1, thence blending into lighter yellow (near Lemon Yellow 4/2 with the tip ⅓ being still lighter yellow (near Lemon Yellow 4/3).

*Intermediate petal.*—Outside surface similar to outside petal. Inside surface similar to outside petal.

*Inner petal.*—Outside surface — similar to intermediate petal; inside surface — similar to intermediate petal. General color effect; newly opened flowers — medium yellow. Three days open — color yellow; less intense. Behavior — opens well in all weather. Spent petals or flowers drop off. Flower longevity (July–August 1987) — plant outdoors in ground; 3–4 days or longer. In cooler weather 4–5 days or longer.

Reproductive organs:

*Stamens.*—Numerous; yellow.

*Filaments.*—Short; yellow.

*Anthers.*—Numerous.
*Pollen.*—Some but so far non-fertile.
*Pistils.*—Fair number.
*Styles.*—Short; yellow; bunched.
*Ovaries.*—All enclosed in calyx.
*Hips.*—None.
*Sepals.*—Permanent; spear shaped; recurved.
*Seeds.*—None.

Foliage:

*Leaves.*—Compound of seven (sometimes nine) leaflets; medium large; leathery; semi-glossy to matt.

*Leaflets.*—Shape: broad, lanceolate; apex acute; base — usually rounded. Color: medium green; new growth — normal (medium green). Rachis: medium strength; upperside may have a few very short hairs; grooved; underside may have several small thorns (or claws) and few short prickles. Stipules: medium to short length; medium (to wide) width; short length narrow points which turn out usually at about 45 degrees or more.

Growth:

*Habit.*—Bushy; rounded; much branched; spreading.

*Growth.*—Vigorous; internodes medium.

*Canes.*—Medium to strong; sturdy.
*Main stems.*—Color: medium green.
*Thorns.*—Numerous, of varying size and length — hooked downward. Hairs — few or none.

The shrub rose plant and its flowers as herein described may vary in slight detail due to climatic, soil and cultural conditions under which the variety may be grown; the present description being of the variety as grown at Visalia, Calif.

The following is claimed:

1. A new and distinct variety of Hybrid Rugosa (shrub) rose plant of hardy, bushy, rounded, much branched habit, substantially as illustrated and described, characterized by buds and flowers of soft to medium yellow color, the bud being pointed in the early opening stage, resembling in form Orangeade (Floribunda—not patented), with the open flower being fairly double, generally of cupped form, with 20–30 or more petals; and further characterized by a plant of compact, vigorous, well rounded shape, with main stems and shoots quite thorny, the said plant being easy to propagate by budding and from soft wood cuttings with an abundance of medium to large semi-glossy to matt foliage, the flowers being borne in clusters on short stems and on tips of new shoots.

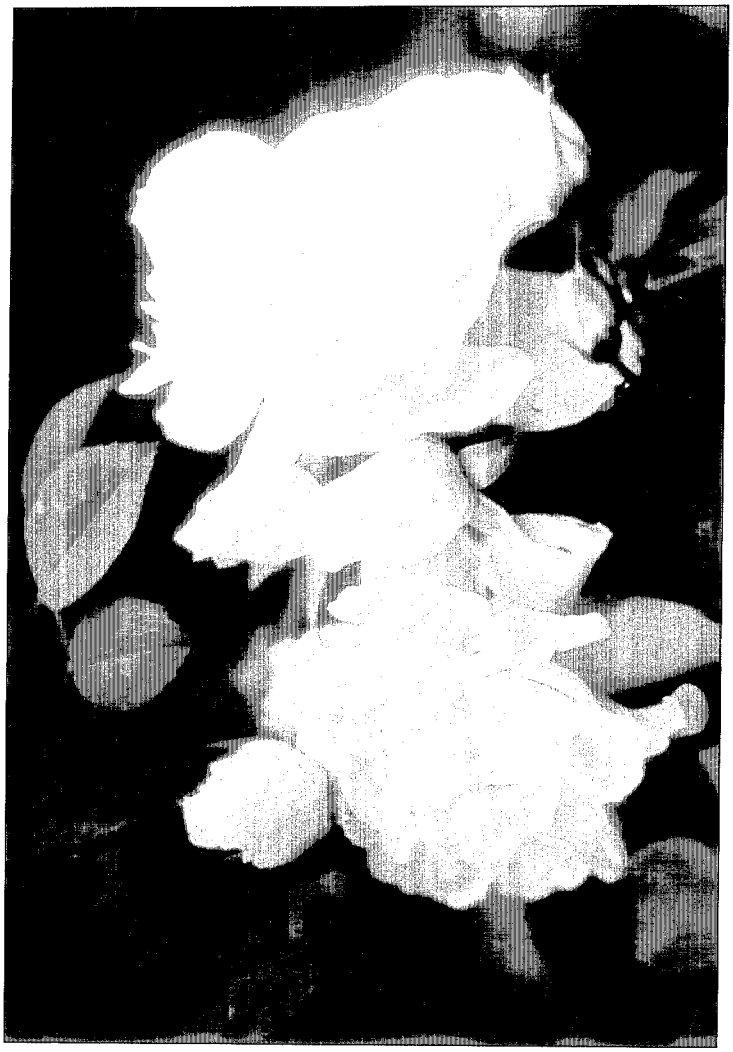

* * * * *